Figure 1:
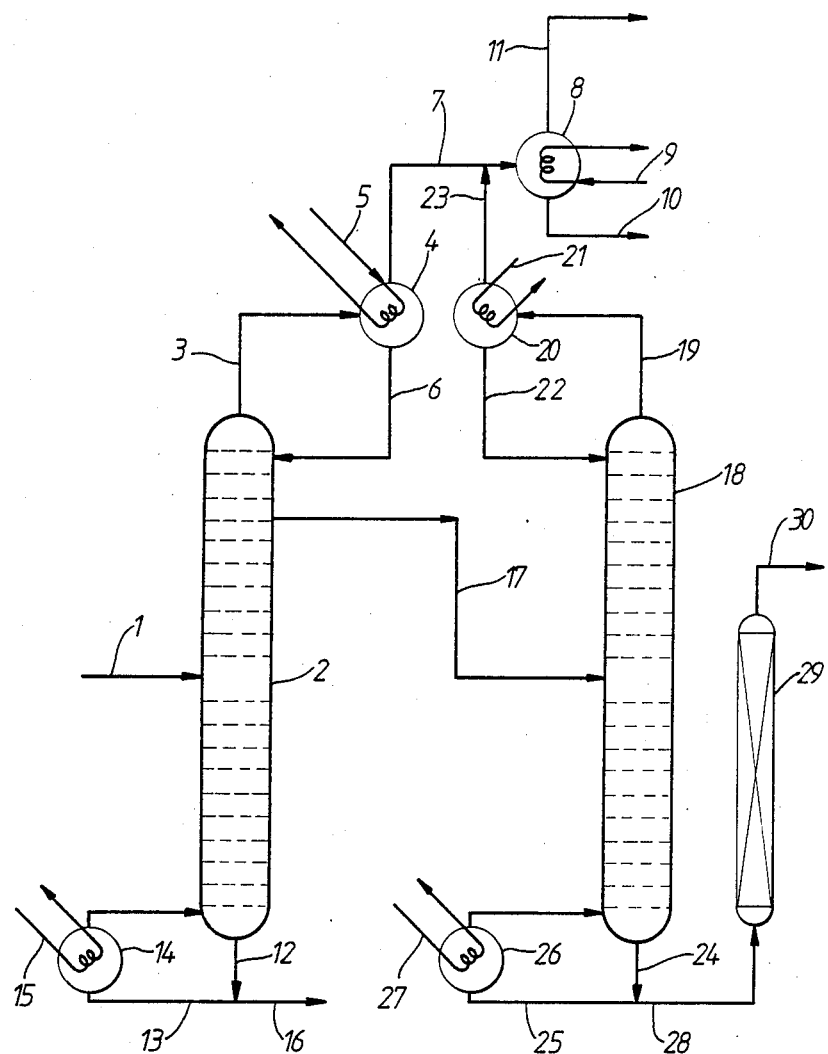

United States Patent [19]

Harris et al.

[11] Patent Number: 4,765,869
[45] Date of Patent: Aug. 23, 1988

[54] PROCESS FOR THE PRODUCTION OF A DIALKYL MALEATE

[75] Inventors: Norman Harris, Norton; Colin Rathmell, Yarm; Keith Turner, Stockton-on-Tees; John Scarlett, Spennymoor, all of England

[73] Assignee: Davy McKee (London) Limited, London, England

[21] Appl. No.: 80,058

[22] Filed: Jul. 31, 1987

[30] Foreign Application Priority Data

Aug. 1, 1986 [GB] United Kingdom ............... 8618892

[51] Int. Cl.⁴ .................... B01D 3/14; C07C 67/54
[52] U.S. Cl. ................................. 203/28; 203/33; 203/37; 203/38; 203/71; 203/77; 203/87; 203/DIG. 19; 560/191
[58] Field of Search ............... 203/28, 33, 37, 38, 203/29, 71, 74, 77, 81, 84, 87, 99, DIG. 19; 560/191, 190, 204; 568/864

[56] References Cited

U.S. PATENT DOCUMENTS

| | | | |
|---|---|---|---|
| 2,333,666 | 11/1943 | Moore et al. | 560/190 |
| 2,938,837 | 5/1960 | Meyer et al. | 203/77 |
| 3,681,204 | 8/1972 | Mercier | 203/77 |
| 3,979,443 | 9/1976 | Schwartz et al. | 560/204 |
| 4,032,458 | 6/1977 | Cooley et al. | 560/190 |
| 4,361,710 | 11/1982 | Weitz et al. | 568/864 |
| 4,562,283 | 12/1985 | Schnabel et al. | 560/204 |
| 4,584,419 | 4/1986 | Sharif et al. | 568/864 |

FOREIGN PATENT DOCUMENTS 143634  6/1985  European Pat. Off. .

| | | | |
|---|---|---|---|
| 54-24818 | 2/1979 | Japan | 560/190 |
| 03189 | 6/1986 | PCT Int'l Appl. . | |
| 07358 | 12/1986 | PCT Int'l Appl. . | |
| 1245568 | 7/1986 | U.S.S.R. | 560/190 |

OTHER PUBLICATIONS

*Chemical Abstracts,* vol. 67, No. 25, Dec. 18, 1967, p. 10964, Abst. #116,520g; Gordinskii, B. Y. et al, "Prepar. and Separation of the Monoalkyl Maleates".

*Primary Examiner*—Wilbur Bascomb
*Attorney, Agent, or Firm*—Bernard, Rothwell & Brown

[57] ABSTRACT

A continuous process is described for the production of a substantially acid free dialkyl maleate, for example diethyl maleate, from a feed stream containing a major amount of dialkyl maleate and a minor amount of the corresponding monoalkyl maleate. This comprises continuously distilling the feed stream in a primary distillation zone, which can comprise a single distillation column or a series of distillation columns connected in series, so as to give (i) a bottom fraction containing monoalkyl maleate and dialkyl maleate in admixture, (ii) a vaporous fraction comprising alkanol, and (iii) an intermediate fraction that is substantially free from alkanol and comprises a major proportion of diethyl maleate and a minor proportion of maleic anhydride. The intermediate fraction (iii) is redistilled in a secondary distillation zone to yield (i) an overhead fraction containing maleic anhydride and (ii) a bottom fraction containing substantially acid free dialkyl maleate. The vaporous stream can be condensed to recover alkanol for recycle to a dialkyl maleate production facility.

21 Claims, 5 Drawing Sheets

PROCESS FOR THE PRODUCTION OF A DIALKYL MALEATE

This invention relates to a process for the production of a dialkyl maleate. In particular it relates to a process for the production of a substantially acid free dialkyl maleate, for example diethyl maleate, from a reaction product containing a major amount of dialkyl maleate and a minor amount of monoalkyl maleate.

The production of dialkyl maleates by esterification of maleic anhydride, of maleic acid or of a mixture containing both maleic anhydride and maleic acid has been described on many occasions in the literature. As maleic acid is dibasic, esterification proceeds stepwise via the monoalkyl maleate. In the case of maleic anhydride this stepwise esterification can be described by the equations:

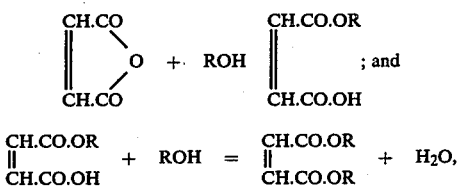

where R is an alkyl group. These reactions can be carried out in two substantially separate steps in separate reactors or simultaneously in a single reactor. The monoesterification step of equation (1) can be effected non-catalytically, conveniently by use of elevated temperatures. The diesterification step of equation (2) can likewise be carried out non-catalytically; however, it is usually preferred to use an esterification catalyst in the diesterification step of equation (2), such as an acid catalyst (e.g. sulphuric acid).

The diesterification step of equation (2) above is a reversible reaction and yields an equilibrium mixture which contains a minor amount of monoalkyl maleate. Many batch methods utilise an added esterification catalyst, such as sulphuric acid. In order to recover the dialkyl maleate product the catalyst must first be removed, prior to attempting purification by distillation techniques, by neutralisation with alkali and then washing with water. These neutralisation steps produce significant quantities of aqueous liquors and remove not only the catalyst but also any monoalkyl maleate and any other acid materials present, such as traces of unreacted maleic anhydride or maleic acid. Although it would be theoretically possible to recover such monoalkyl maleate from the resulting aqueous liquors and to recycle this to the process for the production of further dialkyl maleate, this is not economically feasible. Hence the monoalkyl maleate is lost to the process in these aqueous liquors which are a potential pollution hazard. Moreover the loss of monoalkyl maleate and disposal of these waste liquors represent a significant operating cost.

Various proposals which avoid the use of catalysts have been described. Thus U.S. Pat. No. 4,361,710 proposes washing a gaseous mixture containing maleic anhydride with a monohydric or polyhydric alcohol boiling above 180° C. (e.g. 2-ethylhexanol or dodecan-1-ol) to form a solution of the corresponding maleic acid half-ester in the alcohol followed by heating the solution to remove water and to form a solution of maleic acid diester in the alcohol. As water boils at a temperature well below that of the alcohol it is readily removed from the reaction mixture, thus enabling the diesterification reaction to be driven to completion.

U.S. Pat. No. 4,032,458 describes a process for the production of 1,4-butane diol in which maleic acid is esterified at elevated temperature and pressure and then subjected to a two step hydrogenation procedure. According to the description of the drawing it is preferred to use for esterification a monohydric alcohol which forms a heterogeneous azeotrope with water, such as n-butanol. The esterification step is carried out in a distillation zone from which an n-butanol-water azeotrope is removed overhead. According to column 11, lines 23 to 27, this azeotrope is condensed and allowed to separate into two layers. The n-butanol layer is decanted, redistilled, and recycled to the distillation zone. The n-butanol-water azeotrope has a boiling point (92.7° C. at atmospheric pressure) which is appreciably lower than the boiling point of the alcohol itself (117.4° C. at atmospheric pressure), thus permitting the water to be removed readily from the esterification mixture. In addition the process can only operate as described because the condensed azeotrope is heterogeneous and separates into two layers, thus permitting ready recovery of n-butanol for recycle to the process.

Although it is stated at column 8, lines 45 to 47 of U.S. Pat. No. 4,032,458 that:

"Other suitable monohydric alcohols useful in the process of their invention include ethanol, propanol, butanol, amylalcohol and the like", the illustrated form of plant will not operate with ethanol in place of n-butanol because ethanol is fully miscible with water and forms therewith a homogeneous azeotrope comprising a single liquid phase. It requires much energy to produce substantially dry ethanol from this azeotrope for recycle to the process. Moreover, because the boiling point of the ethanol-water azeotrope is extremely close (78.17° C. at atmospheric pressure) to that of ethanol itself (78.32° C. at atmospheric pressure) all the ethanol must be distilled out of the esterification mixture in order to remove all the water. n-propanol gives rise to similar problems. Because of these factors it is extremely costly in energy requirements, when using ethanol or propanol in the distillation-esterification step of the process of U.S. Pat. No. 4,032,458, to remove the water of esterification completely and hence drive the esterification reaction towards production of a 100% yield of dialkyl maleate.

U.S. Pat. No. 4,562,283 discloses a method of separating maleic anhydride from gaseous reaction mixtures by contact in the bottom of a column with butanol and then washing the treated gases in the column with a counter current stream of butyl maleate. According to column 2, lines 33 to 36 of U.S. Pat. No. 4,562,283, any water formed is removed from the column above the feed point for the butanol. Again, this procedure can be used for removal of the water of esterification only because the butanol-water azeotrope boils appreciably below butanol itself and because the azeotrope separtes into two liquid phases upon condensation.

Copending U.S. application Ser. No. 602,993 describes an alternative to using non-catalytic esterification methods to produce dialkyl maleates or to using homogeneous esterification catalysts such as sulphuric acid. The described method employs a two stage esterification in which the first stage is non-catalytic and the second stage employs an acidic ion exchange resin containing sulphonic acid groups, such as "Amberlyst 16". An impure diethyl maleate product stream is produced which contains diethyl maleate, monoethyl maleate, ethanol and water. Although the use of heterogeneous catalysts obviates use of a neutralisation step for catalyst removal and hence obviates consequent loss of monoalkyl maleate, the problem of incomplete esterification remains, particularly when ethanol is used for esterification. Although a certain degree of purification of the reaction product can be achieved by distillation, it is impossible to obtain pure diethyl maleate in this way because any monoethyl maleate present tends to undergo thermal decompostion under temperature and pressure conditions encountered in the distillation column to yeield maleic anhydride and ethanol. The resulting maleic anhydride contaminates the diethyl maleate fraction. It is possible to reduce this problem by utilising a multi-step esterification procedure for the diesterification reaction in which at least the final stage diesterification involves reaction of the final traces of monoethyl maleate with a large excess of dry ethanol. However the cost of producing dry ethanol represents a significant processing cost.

It would accordingly be desirable to provide a process for the production of a dialkyl maleate from reaction mixtures containing a major amount of dialkyl maleate and a minor amount of monoalkyl maleate in which the difficulties associated with thermal decomposition of monoalkyl maleates are obviated. It would be particularly desirable to provide such a process which can be used for diethyl maleate and for dialkyl maleates derived from other alkanols which form homogeneous azeotropes with water, such as n-propanol.

The present invention accordingly seeks to provide a process for the production of a substantially acid free dialkyl maleate, e.g. diethyl maleate, from a reaction mixture containing a major amount of dialkyl maleate and a minor amount of the corresponding monoalkyl maleate, which process minimises reaction losses arising through use of a neutralisation step and yet substantially overcomes the problems associated with thermal decomposition of the monoalkyl maleate during distillation.

According to the present invention there is provided a continuous process for the production of a substantially acid free dialkyl maleate from a feed stream containing a major amount of dialkyl maleate and a minor amount of monalkyl maleate which comprises:
(a) continuously supplying the feed stream to a primary distillation zone;
(b) continuously distilling the feed stream in the primary distillation zone, thereby inducing thermal decomposition of monoalkyl maleate to yield maleic anhydride and alkanol;
(c) recovering from the primary distillation zone (i) a bottom fraction containing monoalkyl maleate and dialkyl maleate in admixture, (ii) a vaporous fraction comprising alkanol, and (iii) an intermediate fraction which is substantially free from alkanol and which comprises a major proportion of dialkyl maleate and a minor proportion of maleic anhydride;
(d) continuously redistilling the intermediate fraction (iii) from step (c) in a secondary distillation zone to yield (i) an overhead fraction containing maleic anhydride and (ii) a bottom fraction containing substantially acid free dialkyl maleate; and
(e) recovering the bottom fraction (ii) of step (d).

The term "bottom fraction" as used herein means in each case a fraction recovered from a lower part of the respective distillation zone, either in the form of a vaporous stream, which is usually subsequently condensed to form a liquid, or in the form of a liquid stream. The term "intermediate fraction" as used herein, refers not only to a fraction which is withdrawn from the column at a point between the bottom fraction and the overhead fraction, but also includes a fraction which is obtained as a condensate upon partial condensation of the vaporous overhead stream from the distillation column.

The dialkyl maleate is preferably derived from an alkanol, preferably a primary or secondary alkanol, contains up to 4 carbon atoms. The process of the invention is of particular applicability to dialkyl maleates derived from $C_2$ to $C_4$ alkanols, such as ethanol, n-propanol, iso-propanol, n-butanol, iso-butanol and sec-butanol. The process of the invention is accordingly applicable to purification of mixtures containing a major amount of diethyl maleate, di-n-propyl maleate, di-iso-propyl maleate, di-n-butyl maleate, di-iso-butyl maleate, or di-sec-butyl maleate, and a minor amount of the corresponding monoalkyl maleate. The process is used to especial advantage in the production of substantially acid free diethyl maleate from crude mixtures containing a major amount of diethyl maleate and a minor amount of monoethyl maleate.

The feed stream is preferably obtained by esterification of maleic acid, of maleic anhydride, or of a mixture of maleic anhydride and maleic acid with an alkanol, such as ethanol, in one or more stages in the presence of a solid heterogeneous esterification catalyst, such as an ion exchange resin containing acid groups selected from sulphonic acid and carboxylic acid groups. The crude reaction mixture obtained by such a procedure can be used as such in the process of the invention. Preferably, however, the crude reaction mixture is distilled to remove at least a major part of any alkanol and water present therein. In some cases the maleic acid or anhydride feedstock may optionally contain a minor amount (e.g. from about 0.001 mole % up to about 5 mole %) of fumaric acid if the presence of a minor amount of dialkyl fumarate can be tolerated in the resulting substantially acid free dialkyl maleate product; for example, the presence of minor amounts of diethyl fumarate in a diethyl maleate feedstock can be tolerated in the hydrogenation processes described in EP-A-No. 01 43 634, WO-A-No. 86/03189, and WO-A-No. 86/07358. For the avoidance of doubt references hereafter to maleic acid, to monoalkyl maleates and to dialkyl maleates are intended to refer, where the context so permits, not only to the named compounds but also to mixtures of the named compounds and minor amounts of the corresponding fumaric acid, monoalkyl fumarate and/or dialkyl fumarate.

The composition of the feed stream will depend upon the reaction conditions used in its preparation. When esterifying maleic anhydride with ethanol with a view to producing diethyl maleate, for example, it is in practice economically unattractive to attempt to esterify all monoethyl maleate present in the crude esterification mixture. Hence the feed stream generally includes at least about 2 mole % up to about 40 mole % of monoalkyl maleate. Preferably the starting material does not contain more than about 30 mole % of monoalkyl maleate. There can thus be contemplated for use in the process of the invention feed streams containing from about 98:2 to about 60:40 dialkyl maleate:monoalkyl maleate on a molar basis, preferably from about 98:2 to about 70:30 on this basis. Besides dialkyl maleate and monoalkyl maleate the feed stream may also include minor amounts of water and alkanol.

If desired, the bottom fraction (ii) of step (d) can be subjected, after recovery thereof in step (e), to a final neutralisation step to remove any remaining trace of acidic materials, such as maleic anhydride, maleic acid, fumaric acid, monoalkyl maleate, and/or monoalkyl fumarate. Generally speaking the bottom fraction (ii) of step (d) contains no more than about 0.2 to 0.3 mole % in total of acidic materials. Such a neutralisation step conveniently comprises passage of the bottom fraction (ii) of step (d) of the process, possibly after addition of a minor amount of water thereto, through a bed of a basic anion exchange resin, for example a weakly basic anion exchange resin containing substituted amino groups (e.g.—$N(CH_3)_2$ groups), or through a bed of a solid alkali, such as sodium hydroxide or sodium bicarbonate, followed by redistillation. Alternatively it can comprise washing with an aqueous alkaline wash liquor, such as a solution of a mixture of sodium carbonate and disodium maleate (optionally followed by a water wash), and subsequent redistillation to separate water as an overhead product, pure dialkyl maleate as an intermediate product and a sodium containing bottom product. As traces only of acid materials remain in the bottom fraction (ii) of step (d), relatively small amounts only of waste wash liquors are produced in the process of the invention whose disposal does not represent a major problem. Moreover losses of potential dialkyl maleate in the form of monoalkyl maleate, maleic acid or maleic anhydride lost in the waste liquors, are minimal.

In an alternative preferred process according to the invention the acid content of the fraction (ii) of step (d) is reduced still further by repeating the process of the invention utilising said fraction (ii) of step (d), after recovery thereof in step (e), as the feed stream to a further primary distillation zone and thereafter repeating steps (b) to (e).

It will usually be convenient to operate the primary distillation zone of step (a) under reduced pressure, for example at a pressure of from about 0.03 bar to about 0.33 bar. However, pressures of more than 0.33 bar are not excluded, although it will not normally be desired to use a pressure of more than about 1 bar in the primary distillation zone.

The vaporous fraction (ii) of step (c) generally contains, in addition to a mixture of alkanol and a minor amount of maleic anhydride, possibly also any water present in the feed stream, and also a minor amount of dialkyl maleate.

The design of the primary distillation zone will be dependent to some extent on the composition of the reaction product to be treated. For feed streams containing from about 2 mole % up to about 40 mole % monoalkyl maleate, the primary distillation zone may comprise a single distillation column. For reaction products containing from about 15 mole % up to about 40 mole % monoalkyl maleate it may be preferred to use two distillation columns in series since this can result in a reduction in operating costs; in this case the material supplied to the second distillation column of the primary distillation zone from the first distillation column thereof comprises a substantially alkanol free fraction that is richer in dialkyl maleate than the feed stream, and the intermediate fraction (iii) of step (c) is recovered from the second distillation column.

When the primary distillation zone comprises a single distillation column, the intermediate fraction (iii) of step (c) may comprise a vaporous stream taken from a part of the column intermediate the top and bottom thereof. It is also envisaged that the primary distillation zone may comprise a single distillation column provided with a reflux condenser in the path of a vaporous overhead stream therefrom, which reflux condenser is operated under partial condensation conditions so as to produce a substantially alkanol free condensate that contains dialkyl maleate and maleic anhydride; a part of this condensate can be returned as a reflux stream to the column, while the vaporous fraction (ii) of step (c) is recovered from the reflux condenser, and the intermediate fraction (iii) of step (c) comprises another part of the condensate.

When the primary distillation zone comprises first and second distillation columns connected in series, a vaporous stream can be taken from a part of the first distillation column intermediate the top and bottom thereof for supply to the second distillation column, and the intermediate fraction (iii) of step (c) can be recovered from the second distillation column.

Alternatively the primary distillation zone may comprise first and second distillation columns connected in series, in which case the first distillation column may be provided with a reflux condenser in the path of an overhead vaporous fraction therefrom, which reflux condenser is operated under partial condensation conditions so as to produce a substantially alkanol free condensate that comprises dialkyl maleate and maleic anhydride; a part of this condensate from the reflux condenser of the first distillation column can then be returned as a reflux stream to the first distillation column, while a vaporous stream containing alkanol is recovered from the reflux condenser of the first distillation column, and another part of the condensate from the reflux condenser of the first distillation column is supplied to the second distillation column.

When the process involves use of a primary distillation zone comprising first and second distillation columns connected in series, the intermediate fraction (iii) of step (c) may comprise material recovered in vapour form from a part of the second distillation column intermediate the top and bottom thereof. Alternatively the second distillation column may be provided with a reflux condenser in the path of an overhead vaporous stream therefrom, in which case the reflux condenser of the second distillation column can be operated under partial condensation conditions so as to produce a substantially alkanol free condensate that comprises dialkyl maleate and maleic anhydride, a part of the condensate from the reflux condenser of the second distillation column being returned as a reflux stream to the second distillation column, while a vaporous stream containing alkanol is recovered from the reflux condenser of the second distillation column, and the intermediate fraction (iii) of step (c) comprises another part of the condensate from the reflux condenser of the second distillation column.

Preferably the vaporous fraction (ii) of step (c) is subjected to condensation conditions to condense condensible materials, including alkanol, therefrom.

The partial condensation conditions used in certain of these preferred processes result in production of a condensate containing dialkyl maleate, e.g. diethyl maleate, and maleic anhydride and a vaporous stream containing alkanol. Such partial condensation conditions include use of a condensation temperature which is higher than the boiling point of the alkanol or of any alkanol-water azeotrope yet lower than the boiling point of maleic anhydride at the pressure prevailing in the primary distillation zone and which is also higher than the melting point of maleic anhydride (60° C.). Hence the partial condensation conditions include use of a temperature of at least about 60° C. whatever the pressure prevailing in the primary distillation zone. When atmospheric pressure prevails in the primary distillation zone the partial condensation conditions include use of a temperature in the range of from about 80° C. to about 180° C. At lower pressures a lower temperature range may be used. For example at about 0.03 bar the temperature range may be from about 60° C. to about 140° C., while at 0.33 bar it may be from about 60° C. to about 160° C.

The secondary distillation zone of step (d) may comprise a single distillation column which will usually be operated under reduced pressure, for example at a pressure of from about 0.03 bar to about 0.33 bar. However it may alternatively comprise two or more distillation columns in series. The bottom fraction of step (d) is recovered from a lower part of the distillation column of the secondary distillation zone, if this consists of a single distillation column, or from a lower part of the last of the distillation columns in the series, if the secondary distillation zone consists of two or more distillation columns in series, either in the form of a vaporous stream or in the form of a liquid stream; in the former case the vaporous stream is generally condensed to form a liquid stream in the recovery step (e) of the process.

In order that the invention may be clearly understood and readily carried into effect five preferred forms of plant for the purification of impure diethyl maleate feedstreams which operate according to the process of the invention will now be described, by way of example only, with reference to the accompanying drawings, FIGS. 1 to 5 of which are each a flow diagram of the respective plant.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like would additionally be required in a commercial plant. The provision of such ancillary items of equipment forms no part of the present invention and is in accordance with conventional chemical engineering practice.

Referring to FIG. 1 of the drawings, an impure diethyl maleate feedstream containing diethyl maleate, monoethyl maleate, ethanol, and water, is fed in line 1 to an intermediate point of a primary distillation column 2 operated at a pressure of 0.066 bar. This impure diethyl maleate stream is produced by esterification of maleic anhydride with ethanol in two stages in an esterification plant using non-catalytic conditions in the first, monoesterification stage and an acidic ion exchange resin, such as Amberlyst 16, in the second, diesterification stage. (The word "Amberlyst" is a trade mark). This diesterification stage includes use of a plurality of reactors, the final one of which is supplied with "dry" ethanol from a suitable ethanol dehydration unit. The resulting reaction mixture does not require any neutralisation step to remove catalyst therefrom (because a heterogeneous catalyst has been used) but is subjected to a preliminary distillation step upstream from the plant of FIG. 1 in order to remove substantially all water and ethanol present in the crude reaction product and provide the feed stream of line 1.

An overhead stream containing ethanol and minor amounts of water, maleic anhydride, monoethyl maleate, and diethyl maleate, is recovered overhead in line 3 at a temperature of 140° C. The presence of maleic anhydride in the overhead product in line 3 results, it is thought, from the reversible decomposition of monoethyl maleate in primary distillation column 2 according to the equation:

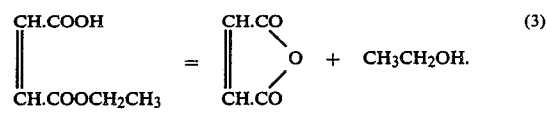

The vapours in line 3 are led through a first condenser 4 which is supplied in line 5 with water under pressure at a temperature of 130° C. A major part of the condensable components of the vapours in line 3 with boiling points above that of ethanol are thereby condensed in first condenser 4. The resulting condensate is returned to primary distillation column 2 in line 6 to form a reflux stream therefor. This condensate consists of a mixture of maleic anhydride, diethyl maleate and monoethyl maleate. A minor part of these higher boiling components in the vapours in line 3 and a major part of the ethanol and water contained therein pass on, still in the vapour form, in line 7 to a second condenser 8 which is supplied in line 9 with chilled cooling medium (e.g. chilled water) so as to cool the vapours to a temperature below 20° C. In this way the residual condensible components present in the vapour stream in line 7 are in large part condensed and losses in the vapour purge are minimised. The resulting condensate contains mainly ethanol and water besides traces of monoethyl maleate, diethyl maleate and maleic anhydride and is recovered in line 10 for recycle to the esterification plant. Line 11 indicates a connection to a vacuum pump or steam ejector (not shown).

A liquid bottom product containing a mixture of diethyl maleate and monoethyl maleate is recovered from primary distillation column 2 in line 12. Part of this liquid bottom product is recycled in line 13 to column reboiler 14 which is supplied with steam in line 15, while the remainder is recycled to the esterification plant in line 16.

An intermediate fraction is recovered from primary distillation column 2 in line 17. This intermediate fraction consists of a major amount of diethyl maleate and a minor amount of maleic anhydride. It is fed to an intermediate point of a secondary distillation column 18. The maleic anhydride present in the stream in line 17 appears overhead in line 19 and is passed to condenser 20 which is fed in line 21 with water at 60° C. The resulting condensate is returned as a reflux stream to column 18 in line 22. Uncondensed maleic anhydride vapour passes on in line 23 and is combined with the stream in line 7 before being recycled to the esterification plant in line 10. The liquid bottom product from secondary distillation column 18 is recovered in line 24 and contains substantially pure diethyl maleate and, at most, only traces (typically about 0.3 mole % or less in total) of acidic materials, such as monoethyl maleate, maleic anhydride and/or maleic acid. Part of this liquid bottom product is recycled in line 25 to column reboiler 26 which is fed with steam in line 27. The remainder is passed in line 28 to neutralisation section 29 where final traces of acid are removed.

A substantially acid free diethyl maleate product stream is recovered in line 30. The compositions and flow rates in the various lines of the plant of FIG. 1 are set out in Table 1.

TABLE 1

|  | LINE NO. | | | | | | |
| --- | --- | --- | --- | --- | --- | --- | --- |
|  | 1 | 7 | 23 | 10 | 16 | 17 | 28 | 30 |
|  | Flow rates in moles per hour | | | | | | |
| Diethyl maleate | 60.3 | 2.0 | 0.8 | 2.8 | 8.3 | 50.0 | 49.2 | 49.2 |
| Monoethyl maleate | 1.5 | Trace | Nil | Trace | 1.1 | 0.1 | Trace | Nil |
| Ethanol | 3.7 | 4.0 | 0.1 | 4.1 | Nil | Nil | Nil | Nil |
| Water | 2.0 | 2.0 | Nil | 2.0 | Nil | Nil | Nil | Nil |
| Maleic anhydride | 0 | Trace | 0.4 | 0.4 | Nil | 0.3 | Trace | Nil |

The overall recovery of diethyl maleate from the feed stream in line 1 is 81.6%. Although there are small losses of acid materials from the plant in the waste liquors from the neutralisation section 29 and possibly also small losses in line 11, the remaining organic material is recovered in lines 10 and 16 and can be recycled to the esterification plant for production of further diethyl maleate.

The results for an alternative feed stream are set out in Table 2 which lists the flow rates and compositions in the most important lines of the plant of FIG. 1.

TABLE 2

|  | LINE NO. | | | | | | |
| --- | --- | --- | --- | --- | --- | --- | --- |
|  | 1 | 7 | 23 | 10 | 16 | 17 | 28 | 30 |
|  | Flow rates in moles per hour | | | | | | |
| Diethyl maleate | 52.0 | 3.0 | 3.0 | 6.0 | 7.8 | 41.2 | 38.2 | 38.2 |
| Monoethyl maleate | 14.2 | Trace | Nil | Trace | 8.3 | 1.4 | * | Nil |
| Ethanol | 5.8 | 10.3 | 0.4 | 10.7 | Nil | Nil | Nil | Nil |
| Water | 0.4 | 0.4 | Nil | 0.4 | Nil | Nil | Nil | Nil |
| Maleic anhydride | Nil | Trace | 5.5 | 5.5 | Nil | 4.5 | * | Nil |

The acid content in line 28, as indicated by the asterisk (*) in Table 2, totals 0.4 moles per hour. With this feedstock the overall recovery of diethyl maleate is 73.5%. However, apart from any losses of material via line 11 and the small losses from the system of acids materials in the aqueous waste liquors from the neutralisation section, the remaining organic material in the feed stream in line 1 is recovered in lines 10 and 16 and can be recycled for re-use in the esterification plant.

Figure 2:
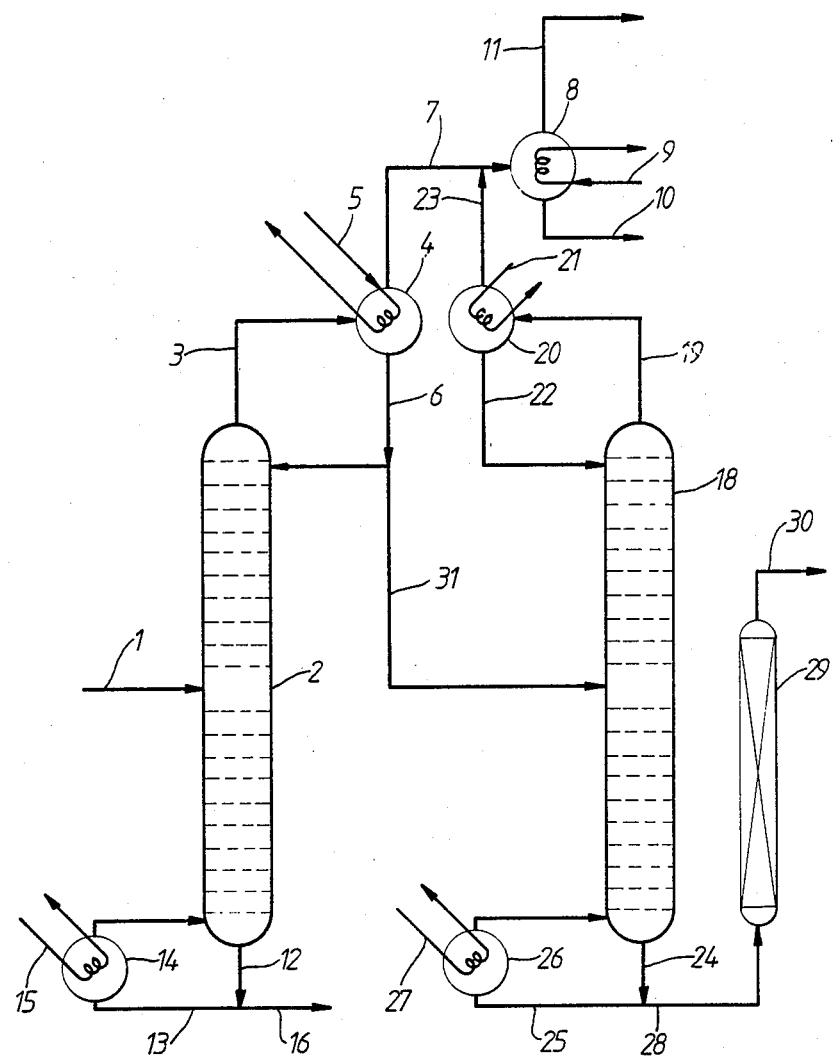

The plant of FIG. 2 is generally similar to that of FIG. 1, except that, instead of taking a vaporous side stream in line 17 to supply the secondary distillation column 18, this is fed by way of line 31 with condensate from line 6.

Figure 3:
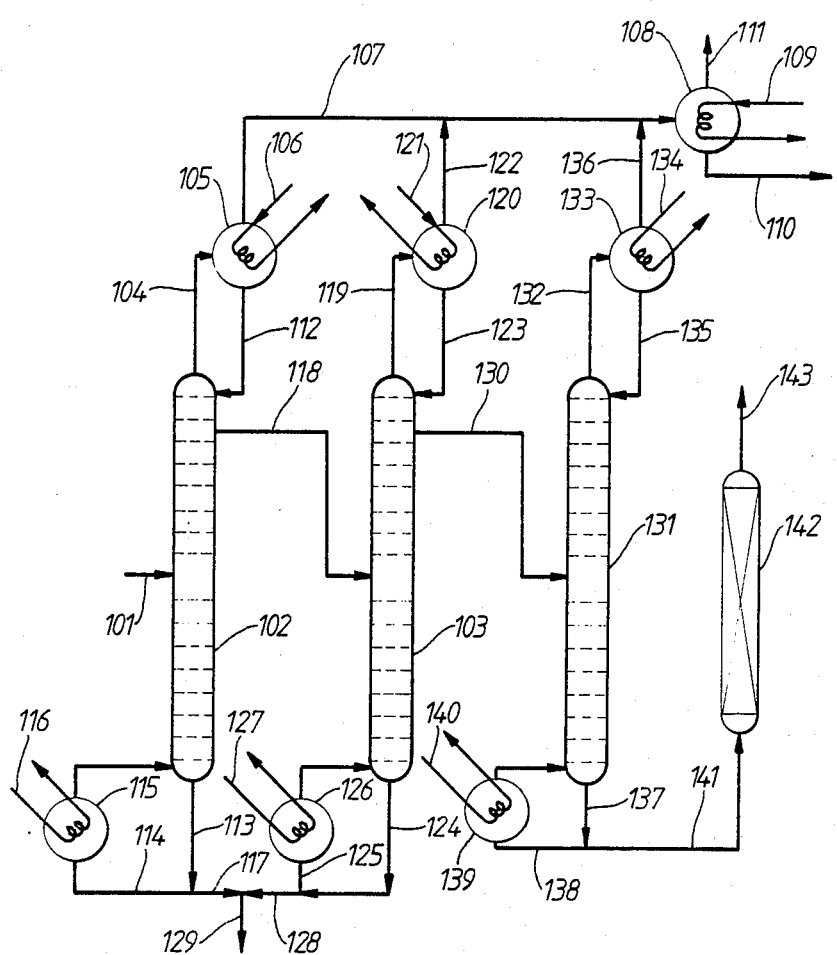

The plant of FIG. 3 is supplied in line 101 with a feed stream containing diethyl maleate, monoethyl maleate, ethanol, and water. This feed stream is obtained by a two step esterification of maleic anhydride with ethanol, using a non-catalytic primary esterification reaction to yield monoethyl maleate followed by addition of ethanol and passage through a single stage diesterification reactor containing a charge of Amberlyst 16 or similar solid esterification catalyst, and then by a preliminary distillation step to remove at least the bulk of the water and ethanol present in the crude reaction product. The feed stream in line 101 is subjected to distillation in a primary distillation zone which includes a first distillation column 102 and a second distillation column 103.

The overhead product from column 102 in line 104 contains ethanol, water, and minor amounts of monoethyl maleate, diethyl maleate and maleic anhydride. This is passed to a condenser 105 which is supplied in line 106 with water at a temperature of 130° C. The operating pressure of column 102 is 0.066 bar.

The ethanol and water, together with traces of monoethyl maleate and diethyl maleate, pass on in line 107 to a condenser 108 which is supplied with chilled cooling medium (e.g. chilled water) at less than 20° C. in line 109. The resulting condensate is recycled to the esterification plant in line 110. Line 111 is a connection to a vacuum pump or a steam ejector (not shown), by means of which the operating pressure in the distillation columns is maintained.

Condensate from condenser 105 is returned as a reflux stream to the top of the first distillation column 102 in line 112.

The liquid bottom product from first distillation column 102 in line 113 contains diethyl maleate and monoethyl maleate. Part of this liquid bottom product is recycled in line 114 to column reboiler 115, which is heated with steam supplied in line 116, and then returned to column 102, while the remainder is recovered in line 117.

An intermediate fraction is recovered in line 118 from first distillation column 102, this intermediate fraction containing a major amount of diethyl maleate and minor amounts of monoethyl maleate and maleic anhydride. It is redistilled in second distillation column 103. The overhead product in line 119 contains ethanol, together with minor amounts of maleic anhydride, monoethyl maleate and diethyl maleate, and is passed to a condenser 120 which is supplied with water under pressure at 130° C. in line 121. Second distillation column 103 is operated at a pressure of 0.066 bar. Uncondensed ethanol vapour, together with traces of monoethyl maleate and diethyl maleate, passes on in line 122 and is combined with the vapours in line 107 for passage through condenser 108. The condensate from condenser 120 is returned to the top of second distillation column 103 as a reflux stream in line 123.

The liquid bottom product from second distillation column 103 is recovered in line 124 and contains diethyl maleate and monoethyl maleate. Part of this liquid bottom product is recycled to column 103 by way of line 125 and column reboiler 126, which is fed with steam in line 127; the remainder is recovered in line 128. The streams in lines 117 and 128 are combined in line 129 and recycled to the esterification plant.

An intermediate fraction is recovered from second distillation column 103 in line 130. This is essentially free from monoethyl maleate and consists of a mixture of a major amount of diethyl maleate and a minor amount of maleic anhydride. This intermediate fraction is fed to a secondary distillation zone in the form of third distillation column 131. Maleic anhydride appears in the overhead product in line 132 which is passed to condenser 133 supplied in line 134 with water at 60° C. Condensate is returned to column 103 as a reflux stream in line 135. Uncondensed vapours pass on in line 136 and are admixed with the vapours in line 107 for passage to the condenser 108. The liquid bottom product in line 137 is a substantially acid free diethyl maleate stream. Part of this bottom product in line 137 is recycled to column 131 in line 138 through reboiler 139, which is fed with steam in line 140. The remainder passes on in line 141 to neutralisation section 142 in which remaining traces of acid are removed. A pure acid free diethyl maleate stream is recovered in line 143.

The compositions and flow rates of the various streams in the most important lines of the plant of FIG. 3 are set out in Table 3.

ible components in line 202 which have boiling points above that of ethanol. The condensate therefrom is returned to column 201 by way of lines 205 and 206 to form a reflux stream therefor. The ethanol passes on in line 207 to a second condenser 208 which is supplied in line 209 with chilled cooling medium (e.g. chilled water) so as to cool the vapours to a temperature below 20° C. In this way the residual condensible components present in the vapour stream in line 207 are in large part condensed and losses in the vapour purge are minimised. The resulting condensate contains mainly ethanol besides traces of monoethyl maleate, diethyl maleate and maleic anhydride and is recovered in line 210 for recycle to column 18. Line 211 indicates a connection to a vacuum pump or steam ejector (not shown).

A liquid bottom product consisting essentially of diethyl maleate and a trace of monoethyl maleate and other acidic materials is recovered from column 201 in line 212. Part of this liquid bottom product is recycled in line 213 to column reboiler 214 which is supplied with steam in line 215, while the remainder is recycled to the esterification plant in line 216.

Part of the condensate in line 205 is fed by way of line 217 to an intermediate point of a further distillation column 218. The majority of any remaining maleic anhydride present in the stream in line 217 appears overhead in line 219 and is passed to condenser 220 which is fed in line 221 with water at 60° C. The result-

TABLE 3

| | LINE NO. | | | | | | | | | | | |
|---|---|---|---|---|---|---|---|---|---|---|---|---|
| | 101 | 107 | 118 | 122 | 136 | 110 | 117 | 128 | 129 | 130 | 141 | 143 |
| | Flow rates in moles per hour | | | | | | | | | | | |
| Diethyl maleate | 49.5 | 3.0 | 41.5 | 0.1 | 3.0 | 6.1 | 5.0 | 5.9 | 10.9 | 35.5 | 32.5 | 32.5 |
| Monoethyl maleate | 16.8 | Trace | 1.2 | Trace | Nil | Trace | 14.5 | 0.7 | 15.2 | 0.4 | Trace | Nil |
| Ethanol | 3.8 | 4.9 | Nil | 0.1 | 0.4 | 5.4 | Nil | Nil | Nil | Nil | Nil | Nil |
| Water | 0.2 | 0.2 | Nil | Nil | Nil | 0.2 | Nil | Nil | Nil | Nil | Nil | Nil |
| Maleic anhydride | Nil | Trace | 1.1 | Trace | 1.6 | 1.6 | Nil | Nil | Nil | 1.2 | Trace | Nil |

Figure 4:
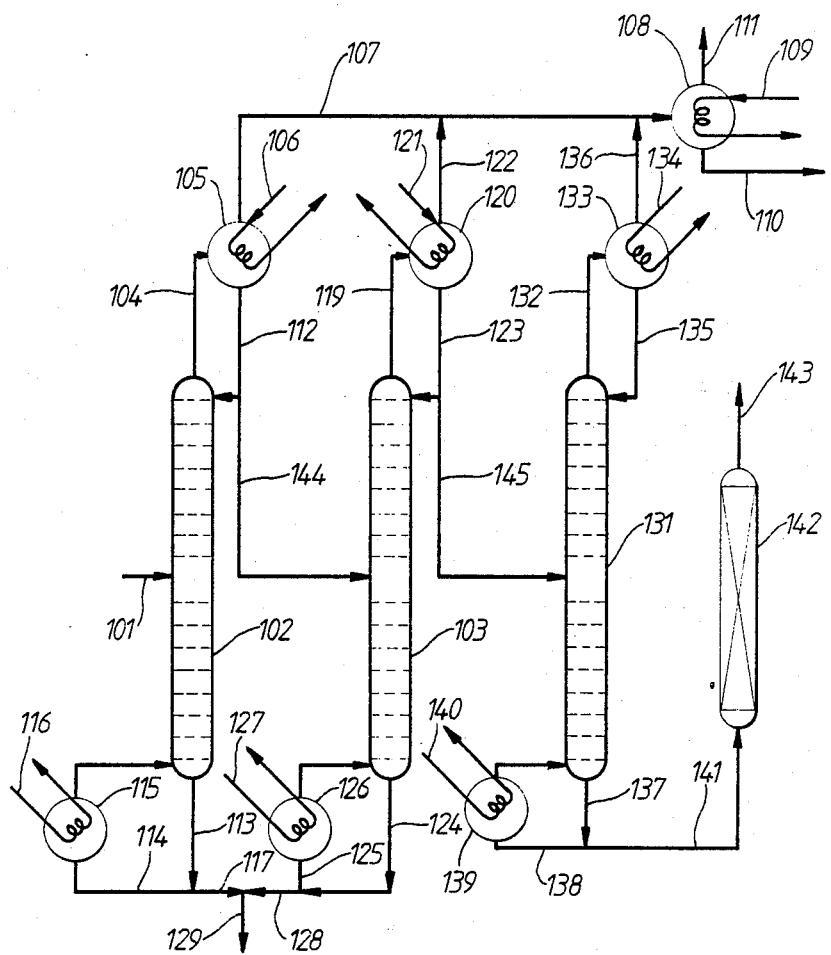

The plant of FIG. 4 is generally similar to that of FIG. 3 except that, instead of taking vaporous side streams in line 118 and 130 from the first and second distillation columns 102 and 103 of the primary distillation zone to supply the second distillation column 103 and the third distillation column 131 respectively, these columns are supplied by way of lines 144 and 145 respectively with condensate from lines 112 and 123 respectively.

Figure 5:
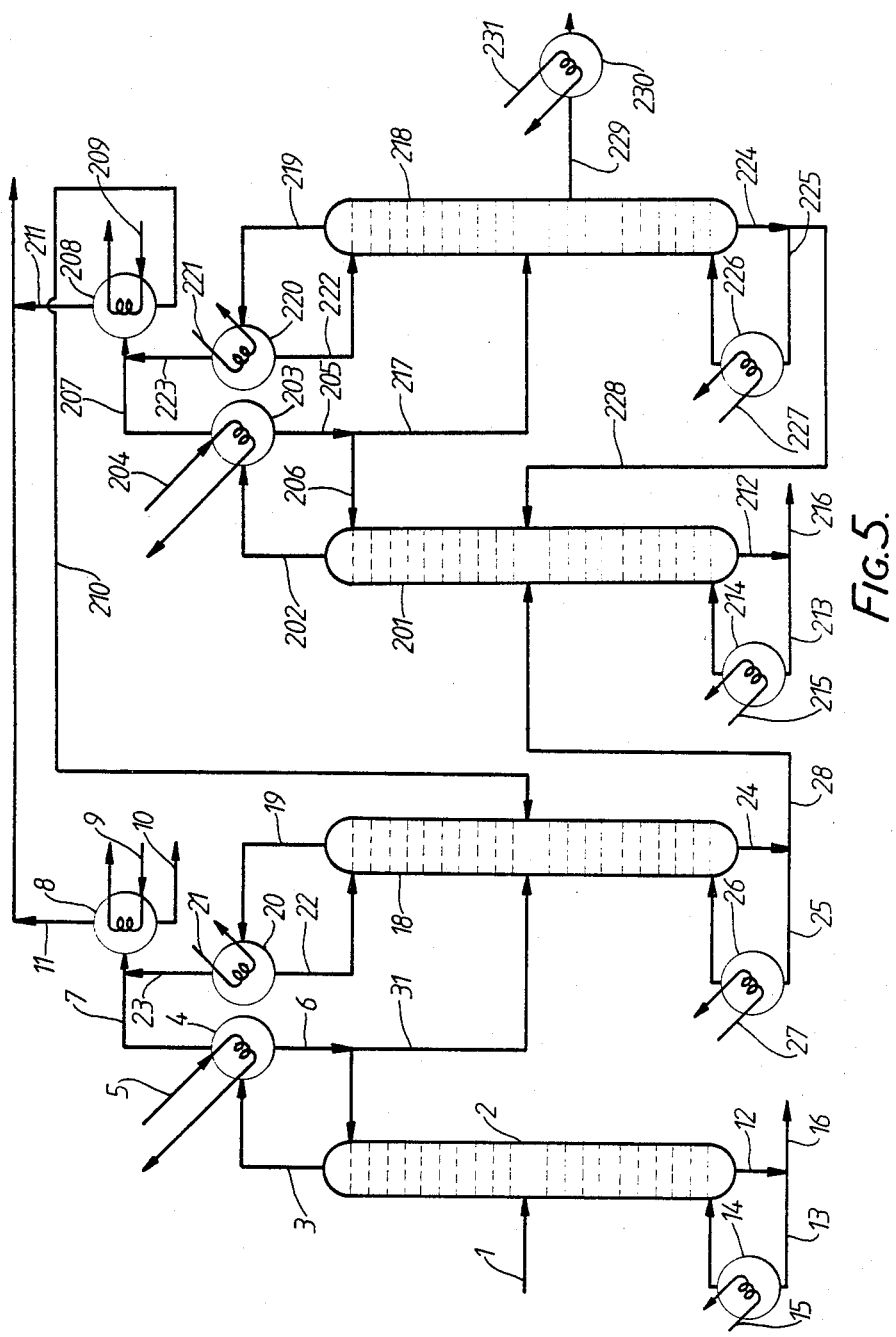

The plant of FIG. 5 is a modified form of the plant of FIG. 2 and like reference numerals have been used to indicate like parts in FIGS. 2 and 5. Instead of passing the material in line 28 to a neutralisation section 29, this is fed to a further primary distillation column 201 which is operated under reduced pressure. The overhead stream in line 202 contains traces of ethanol and maleic anhydride but consists predominantly of diethyl maleate. Condenser 203 is supplied with cooling water in line 204 so as to condense a major part of the condensing condensate, which is predominantly diethyl maleate but contains a trace of maleic anhydride, is returned as a reflux stream to column 218 in line 222. Any uncondensed maleic anhydride vapour passes on in line 223 and is combined with the stream in line 207 before being recycled to column 18 in line 210. A liquid stream is taken from column 218 in line 224. Part of this liquid stream is recycled in line 225 to column reboiler 226 which is fed with steam in line 227. A minor purge stream is recycled in line 228 to column 201.

A vaporous diethyl maleate bottom product stream is recovered from column 218 in line 229 and condensed in condenser 230 whose cooling water supply line is indicated at 231. The compositions and flow rates in the various lines of the plant of FIG. 5 are set out in Table 4, together with some relevant operating conditions. In the case of lines 1, 28, 31, 217 and 228 the conditions mentioned are those at the delivery end of the respective line.

TABLE 4

| | LINE NO. | | | | | | | | | |
|---|---|---|---|---|---|---|---|---|---|---|
| | 1 | 7 | 31 | 23 | 28 | 207 | 217 | 223 | 228 | 229 |
| | Flow rates in kg moles per hour | | | | | | | | | |
| Diethyl maleate | 108.4 | 3.8 | 90.3 | 0.1 | 98.9 | 7.1 | 89.6 | 4.5 | 8.5 | 76.6 |
| Monoethyl maleate | 21.0 | Nil | 0.1 | Nil | 0.1 | Trace | Trace | Nil | Trace | Nil |
| Ethanol | 7.6 | 14.0 | 2.0 | 1.7 | Nil | Trace | Nil | Trace | Nil | Nil |
| Water | 1.9 | 1.7 | 0.2 | 0.2 | Nil | Nil | Nil | Nil | Nil | Nil |
| Maleic anhydride | Nil | 0.9 | 7.5 | 0.5 | Trace | Trace | Trace | Trace | Nil | Nil |
| "Heavies" | 1.9 | Nil | Trace | Nil | Trace | Nil | Nil | Nil | Nil | Nil |
| Temperature (°C.) | 82 | 109 | 109 | 91 | 162 | 148 | 92 | 146 | 162 | 148 |

TABLE 4-continued

| | LINE NO. | | | | | | | | |
|---|---|---|---|---|---|---|---|---|---|
| 1 | 7 | 31 | 23 | 28 | 207 | 217 | 223 | 228 | 229 |
| Pressure (bar) 0.14 | 0.10 | 0.12 | 0.10 | 0.14 | 0.11 | 0.14 | 0.11 | 0.14 | 0.11 |

The plants of FIGS. 1 to 5 have been described in relation to feed streams containing diethyl maleate and monoethyl maleate and the recovery therefrom of substantially pure diethyl maleate. For some purposes, however, the present of a minor amount of diethyl fumarate can be tolerated in the product diethyl maleate; for example, the presence of from about 0.001 mole % up to about 5 mole % diethyl fumarate in the product stream can be tolerated in the process of EP-A-No. 01 43 634, WO-A-No. 86/03189, or WO-A-No. 86/07358. In such cases the feed stream can contain corresponding amounts of diethyl fumarate, besides minor amounts of fumaric acid and/or of monoethyl fumarate, resulting, for example, from the presence of a minor amount of fumaric acid in the maleic anhydride used as feedstock for the production of the diethyl maleate-containing feed stream. Under such circumstances monoethyl fumarate will be present, in addition to monoethyl maleate, in the stream in line 16 or in line 129, while diethyl fumarate will be present in the final product stream in line 30, in line 143, or in line 229 in addition to diethyl maleate. If essentially pure diethyl maleate is required from a product stream in line 30, in line 143, or in line 229, that contains also diethyl fumarate, then this can be obtained from the respective product stream by further distillation.

FIGS. 1 to 5 illustrate the use of distillation columns with trays; it will be appreciated by those skilled in the art that any other suitable form of distillation column can be used, such as packed towers, in place of the illustrated type of column.

What is claimed is:

1. A continuous process for the production of a substantially acid-free dialkyl maleate from a feed stream containing a major amount of dialkyl maleate and a minor amount of monoalkyl maleate which comprises:
   (a) continuously supplying the feed stream to a primary distillation zone;
   (b) continuously distilling the feed stream in the primary distillation zone, thereby inducing thermal decomposition of monoalkyl maleate to yield maleic anhydride and alkanol;
   (c) recovering from the primary distillation zone (i) a bottom fraction containing monoalkyl maleate and dialkyl maleate in admixture, (ii) a vaporous fraction comprising alkanol, and (iii) an intermediate fraction which is substantially free from alkanol and which comprises a major proportion of dialkyl maleate and a minor proportion of maleic anhydride;
   (d) continuously redistilling the intermediate fraction (iii) from step (c) in a secondary distillation zone to yield (i) an overhead fraction containing maleic anhydride and (ii) a bottom fraction containing substantially acid-free dialkyl maleate; and
   (e) recovering the bottom fraction (ii) of step (d).

2. A process according to claim 1, in which the bottom fraction (ii) of step (d) is subjected, after recovery thereof in step (e), to a final neutralisation step.

3. A process according to claim 1, in which the primary distillation zone is operated under reduced pressure in the range of from about 0.03 bar to about 0.33 bar.

4. A process according to claim 1, in which the primary distillation zone comprises a single distillation column and in which the feed stream supplied thereto contains from about 2 mole % to about 40 mole % of monoalkyl maleate and from about 98 mole % to about 60 mole % dialkyl maleate.

5. A process according to claim 1, in which the primary distillation zone comprises a single distillation column and in which the intermediate fraction (iii) of step (c) comprises a vaporous stream taken from a part of the column intermediate the top and bottom thereof.

6. A process according to claim 1, in which the primary distillation zone comprises a single distillation column provided with a reflux condenser in the path of a vaporous overhead stream therefrom, in which the reflux condenser is operated under partial condensation conditions so as to produce a substantially alkanol free condensate that contains dialkyl maleate and maleic anhydride, in which a part of the condensate is returned as a reflux stream to the column, in which the vaporous fraction (ii) of step (c) is recovered from the reflux condenser, and in which the intermediate fraction (iii) of step (c) comprises another part of the condensate.

7. A process according to claim 1, in which the primary distillation zone comprises first and second distillation columns connected in series, in which the feed stream supplied to the first distillation column contains from about 15 mole % to about 40 mole % of monoalkyl maleate, in which the material suplied to the second distillation column from the first distillation column comprises a substantially alkanol free fraction that is richer in dialkyl maleate than the feed stream, and in which the intermediate fraction (iii) of step (c) is recovered from the second distillation column.

8. A process according to claim 1, in which the primary distillation zone comprises first and second distillation columns connected in series, in which a vaporous stream is taken from a part of the first distillation column intermediate the top and bottom thereof for supply to the second distillation column, and in which the intermediate fraction (iii) of step (c) is recovered from the second distillation column.

9. A process according to claim 1, in which the primary distillation zone comprises first and second distillation columns connected in series, in which the first distillation column is provided with a reflux condenser in the path of an overhead vaporous fraction therefrom, in which the reflux condenser of the first distillation column is operated under partial condensation conditions so as to produce a substantially alkanol free condensate that comprises dialkyl maleate and maleic anhydride, in which a part of the condensate from the reflux condenser of the first distillation column is returned as a reflux stream to the first distillation column, in which a vaporous stream containing alkanol is recovered from the reflux condenser of the first distillation column, and in which another part of the condensate from the reflux condenser of the first distillation column is supplied to the second distillation column.

10. A process according to claim 9, in which the intermediate fraction (iii) of step (c) comprises material recovered in vapour form from a part of the second distillation column intermediate the top and bottom thereof.

11. A process according to claim 9, in which the second distillation column is provided with a reflux condenser in the path of an overhead vaporous stream therefrom, in which the reflux condenser of the second distillation column is operated under partial condensation conditions so as to produce a substantially alkanol free condensate that comprises dialkyl maleate and maleic anhydride, in which a part of the condensate from the reflux condenser of the second distillation column is returned as a reflux stream to the second distillation column, in which a vaporous stream containing alkanol is recovered from the reflux condenser of the second distillation column, and in which the intermediate fraction (iii) of step (c) comprises another part of the condensate from the reflux condenser of the second distillation column.

12. A process according to claim 1, in which the vaporous fraction (ii) of step (c) is subjected to condensation conditions to condense condensible materials, including alkanol, therefrom.

13. A process according to claim 1, in which the dialkyl maleate is diethyl maleate, in which the monoalkyl maleate is monoethyl maleate, and in which the alkanol is ethanol.

14. A process according to claim 1, in which the feed stream contains also a minor amount of the corresponding dialkyl fumarate and in which the bottom fraction (ii) of step (d) contains also dialkyl fumarate.

15. A process according to claim 14, in which the feed stream contains from about 0.001 mole % up to about 5 mole % of dialkyl fumarate.

16. A continuous process for the production of a substantially acid free diethyl maleate from a feed stream containing a major amount of diethyl maleate and a minor amount of monoethyl maleate which comprises:
(a) continuously supplying the feed stream to a primary distillation zone;
(b) continuously distilling the feed stream in the primary distillation zone, thereby inducing thermal decomposition of monoethyl maleate to yield maleic anhydride and ethanol;
(c) recovering from the primary distillation zone (i) a bottom fraction containing monoethyl maleate and diethyl maleate in admixture, (ii) a vaporous fraction comprising ethanol, and (iii) an intermediate fraction which is substantially free from ethanol and which comprises a major proportion of diethyl maleate and a minor proportion of maleic anhydride;
(d) continuously redistilling the intermediate fraction (iii) from step (c) in a secondary distillation zone to yield (i) an overhead fraction containing maleic anhydride and (ii) a bottom fraction containing substantially acid free diethyl maleate; and
(e) recovering the bottom fraction (ii) of step (d).

17. A process according to claim 16, in which the primary distillation zone comprises a single distillation column and in which the feed stream supplied thereto contains from about 2 mole % to about 40 mole % of monoethyl maleate and from about 98 mole % to about 2 mole % diethyl maleate.

18. A process according to claim 16, in which the primary distillation zone comprises a single distillation column provided with a reflux condenser in the path of a vaporous overhead stream therefrom, in which the reflux condenser is operated under partial condensation conditions so as to produce a substantially alkanol free condensate that contains dialkyl maleate and maleic anhydride, in which a part of the condensate is returned as a reflux stream to the column, in which the vaporous fraction (ii) of step (c) is recovered from the reflux condenser, and in which the intermediate fraction (iii) of step (c) comprises another part of the condensate.

19. A process according to claim 16, in which the vaporous fraction (ii) of step (c) is subjected to condensation conditions to condense condensible materials, including ethanol, therefrom.

20. A process according to claim 16, which further comprises:
(f) continuously supplying the bottom fraction (ii) of step (d) as a feed stream to a further primary distillation zone;
(g) continuously distilling the bottom fraction (ii) of step (d) in the further primary distillation zone under temperature and pressure conditions conducive to thermal decomposition of monoethyl maleate to yield maleic anhydride and ethanol;
(h) recovering from the further primary distillation zone (i) a bottom fraction containing monoethyl maleate and diethyl maleate in admixture, (ii) a vaporous fraction comprising ethanol, and (iii) an intermediate fraction which is substantially free from ethanol and which comprises a major proportion of diethyl maleate and a minor proportion of maleic anhydride;
(i) continuously redistilling the intermediate fraction (iii) from step (h) in a further secondary distillation zone to yield (i) an overhead fraction containing maleic anhydride and (ii) a bottom fraction containing substantially acid free diethyl maleate, which bottom fraction exhibits a lower acidity than the bottom fraction (ii) of step (d); and
(j) recovering the bottom fraction (ii) of step (i).

21. A process according to claim 20, in which the bottom fraction (ii) of step (i) is recovered in vapour form from a lower part of the further secondary distillation zone.

* * * * *